US006257891B1

(12) United States Patent
Moore et al.

(10) Patent No.: US 6,257,891 B1
(45) Date of Patent: Jul. 10, 2001

(54) APPARATUS AND METHOD FOR CREATING A STRUCTURE WITH COMPLEX EXTERNAL AND INTERNAL SHAPES

(75) Inventors: Tom Moore, Waco; George M. Blackburn, Jr., Austin, both of TX (US)

(73) Assignee: Aqua Innovators Inc., Austin, TX (US)

( * ) Notice: Subject to any disclaimer, the term of this patent is extended or adjusted under 35 U.S.C. 154(b) by 0 days.

(21) Appl. No.: 09/396,283

(22) Filed: Sep. 15, 1999

(51) Int. Cl.[7] .................................................. A61C 5/08
(52) U.S. Cl. ............................ 433/218; 433/34; 433/223
(58) Field of Search ............................... 433/34, 47, 75, 433/213, 214, 218, 223, 74; 264/16, 19

(56) References Cited

U.S. PATENT DOCUMENTS

| | | | |
|---|---|---|---|
| 2,337,036 | * 12/1943 | Erdle | 433/34 X |
| 4,162,625 | * 7/1979 | Simmons | 433/34 X |
| 4,609,511 | 9/1986 | Fischer et al. . | |
| 4,672,081 | 6/1987 | Fisher et al. . | |
| 4,850,871 | 7/1989 | Bryan . | |
| 4,854,875 | 8/1989 | Dziki et al. . | |
| 4,957,441 | 9/1990 | Bryan . | |
| 5,015,180 | 5/1991 | Randklev . | |
| 5,100,317 | * 3/1992 | Darnand | 433/60 |
| 5,207,574 | * 5/1993 | Garland | 433/213 X |
| 5,219,608 | 6/1993 | Aoki et al. . | |
| 5,348,475 | 9/1994 | Waknine et al. . | |
| 5,447,967 | 9/1995 | Tyszblat . | |
| 5,569,033 | * 10/1996 | Michael | 433/213 X |
| 5,575,645 | 11/1996 | Jacobs et al. . | |
| 5,609,483 | * 3/1997 | Thomsen | 433/213 X |
| 5,647,744 | * 7/1997 | Squicciarini | 433/213 X |
| 5,738,518 | * 4/1998 | Nowak | 433/213 X |
| 5,911,580 | 6/1999 | Sharp et al. . | |
| 6,089,863 | * 7/2000 | Van Valey | 433/60 X |

FOREIGN PATENT DOCUMENTS

0269305A1   11/1988   (EP) .
0375161A2   12/1988   (EP) .

* cited by examiner

*Primary Examiner*—Nicholas D. Lucchesi
(74) *Attorney, Agent, or Firm*—J. Nevin Shaffer, Jr.; Shaffer & Culbertson, LLP

(57) ABSTRACT

An apparatus and method for creating a structure (10) with complex external and internal shapes (12 and 14) includes a unitary flexible mold of a structure (10) with complex external shapes (12). A unitary flexible male mold (24) of the interior of the structure with complex internal shapes (14) that mirror the complex external shapes (12) is created. A keying device (42) connected to the molds (16 and 24) is utilized so that the unitary flexible female mold (16) and the unitary flexible male mold (24) are maintained in a predetermined, fixed relationship (40) when pressed together.

20 Claims, 2 Drawing Sheets

US 6,257,891 B1

APPARATUS AND METHOD FOR CREATING A STRUCTURE WITH COMPLEX EXTERNAL AND INTERNAL SHAPES

BACKGROUND OF THE INVENTION

This invention relates to an apparatus and method for creating a structure with complex external and internal shapes. In a preferred embodiment of the invention, the invention relates to an apparatus and method for creating dental crowns with complex external and internal shapes.

A variety of means and methods have been developed over the years for creating structures from molds. A continuing problem is the creation of structures with complex external shapes. The difficulty with preparing molds with complex shapes is that it is difficult to create a mold for complex shapes that is capable of releasing the shape once the material within the mold has hardened. One common solution is to split the mold so as to enable the form to be released after it has hardened.

A much more difficult problem is to create structures with complex external shapes accompanied with complex internal shapes. In fact, to the inventors' knowledge, there is no unitary mold capable of creating a structure with complex external and internal shapes.

In particular, in the field of dentistry, to treat damaged teeth, it is known how to make fairly simple external shapes for crowns. See for example, Updyke, et al., U.S. Pat. No. 5,775,913. Nonetheless, even these simple external shapes require the use of split forms in order to release those simple shapes from the mold. Again, a much more difficult problem, heretofore unsolved as far as the Applicants know, is the creation of not only complex external shapes, but in particular, the creation of complex internal shapes. While the prior art has focused on the creation of reasonably accurate reproductions of the external shapes of teeth, there has been no solution for the creation of the internal portion of a structure, crown, to incorporate complex internal shapes mirroring the complex external shapes found in an actual tooth. In fact, to Applicants' knowledge, the internal structure of the crowns known in the art at best are designed to accommodate a rectangular shaped tooth (see e.g. Updyke, et al., U.S. Pat. No. 5,775,913), and at worst and more typically, a "TP" form. That is to say, the application of crowns in the prior art required the preparation of the diseased or damaged tooth into a shape readily accommodated by the crown and a shape which would allow the removal of the crown in the future. This shape, in the form of a tapering trapezoid from the base to the top of the tooth, is illustrated over and over again in the prior art. (See e.g. Dzilki, et al., U.S. Pat. No. 4,854,875 and Bryan, U.S. Pat. No. 4,850,871) The creation of this traditional TP in dentistry results in the destruction of portions of perfectly healthy teeth in order to accommodate prior art crowns.

Goracci, et al., disclose in the July, 1999 issue of Compendium, in an article entitled "Aesthetic and Functional Reproduction of Occlusal Morphology With Composite Resins", a process for repairing teeth with minor dental decay. This process essentially includes the creation of a mold of the exterior of the tooth prior to removal of the dental decay. The dental decay is removed, then filled and the exterior mold is placed over the tooth until the filling material hardens, at which time the exterior mold is removed. As the authors themselves point out, however, an important limitation of this method is that it can be used only when the occlusal surface of the tooth is not damaged by the carious lesion.

As a result, there is a need in the art for providing an apparatus and method for creating a structure with complex external and internal shapes. It, therefore, is an object of this invention to provide an improved apparatus and method for creating a structure with complex external and internal shapes which does not require single or multiple split molds, which is easy to use, and which is capable of repetitive use for the creation of multiple, essentially identical structures.

SHORT STATEMENT OF THE INVENTION

Accordingly, the apparatus for creating a structure with complex external and internal shapes of the present invention includes a unitary flexible female mold of a complex external shape. A unitary flexible male mold of complex internal shapes and a keying device is provided so that the unitary flexible female mold and the unitary flexible male mold are maintained in a predetermined fixed relationship when pressed together. The invention includes complex shapes in the form of convex and/or concave shapes.

In a preferred embodiment, the unitary flexible female mold is attached to and surrounded by a flexible mounting and the flexible mounting is attached to a rigid support member. Further, in a preferred embodiment, the unitary flexible male mold includes an internal flexible mounting filling which is attached to a rigid support member.

A corresponding method is more fully disclosed and claimed hereafter.

BRIEF DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE PREFERRED EMBODIMENT

Figure 1:
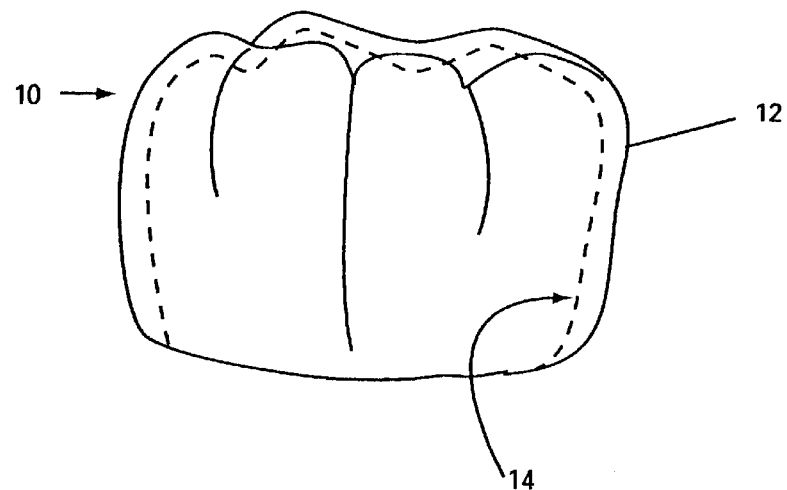
FIG. 1 is a plan view of a hollow structure with complex, convex and concave shapes, the exterior being mirrored by the interior.

The preferred embodiment of the present invention is illustrated by way of example in FIGS. 1–4. Referring specifically to FIG. 1, structure 10 is illustrated. Structure 10, in this example a tooth, has a complex external shape 12 and a corresponding complex internal shape 14 that essentially mirrors the complex external shape 12. For these purposes, the term complex is used to mean a shape that is more than a simple geometric form such as a rectangle, or a rectangle that narrows from bottom to top as is the common form of "TP-ing" a tooth for receiving a crown. Still further, a complex shape, as used herein, includes both convex and concave forms singularly and together.

Figure 2:
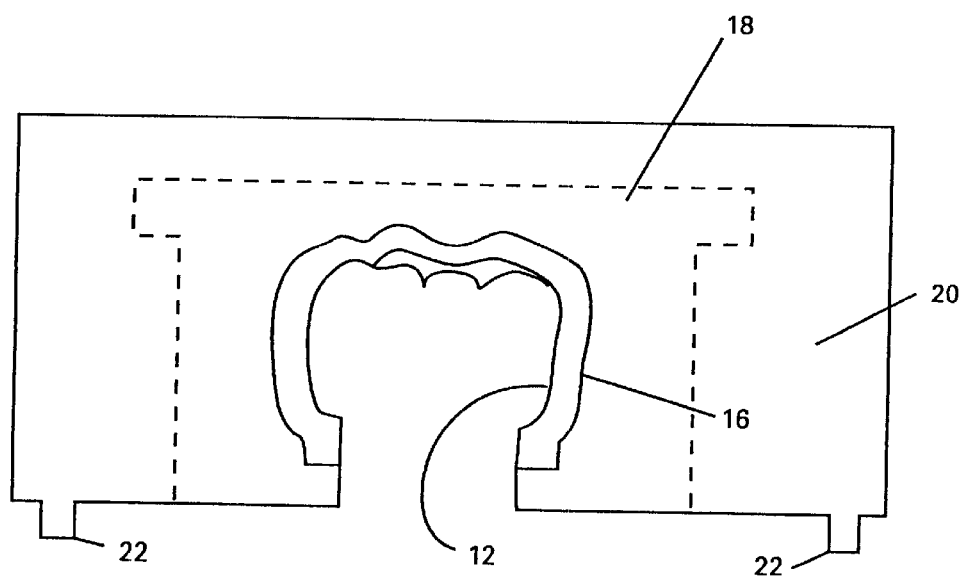
FIG. 2 is a side view of the unitary flexible female mold of the present invention created from the hollow structure illustrated in FIG. 1 and the rigid support for the unitary flexible female mold.
Figure 3:
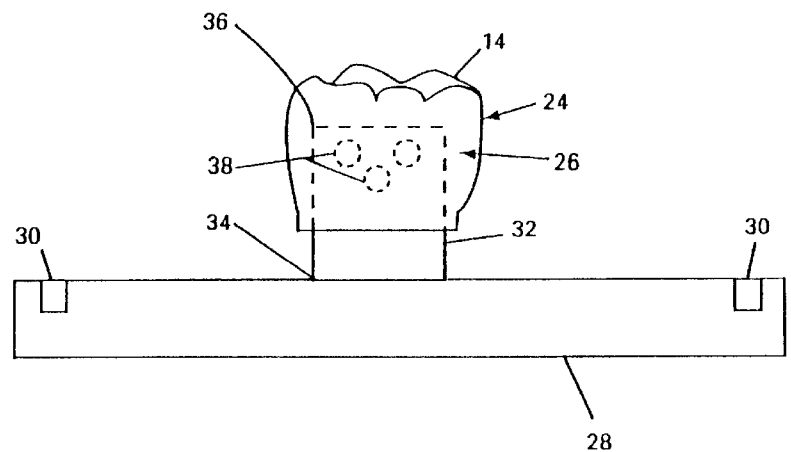
FIG. 3 is a side view of the unitary flexible male mold of the present invention attached to a post which is attached to a rigid support member.

Referring now to FIGS. 2 and 3, FIG. 2 shows unitary flexible female mold 16. Unitary flexible female mold 16 is a mold of structure 10. Structure 10, again, has a complex external shape 12. Unitary flexible female mold 16 is, in a preferred embodiment, a mold of the complex external shape 12 of structure 10.

FIG. 2 also illustrates a preferred embodiment of the invention wherein unitary flexible female mold 16 is surrounded and encased by flexible mounting 18. Also, illustrated in FIG. 2 is rigid support member 20 and extended keys 22.

Referring now to FIG. 3, unitary flexible male mold 24 is illustrated. Unitary flexible male mold 24 is, in a preferred embodiment, a mold of the complex internal shape 14 of structure 10. As can be seen from the illustration, unitary flexible male mold 24 is in the shape of complex internal shape 14 of structure 10 and, once again, complex internal shape 14 essentially mirrors the complex external shape 12.

FIG. 3 also illustrates internal flexible mounting filling 26. Further, rigid support member 28 is illustrated, along with key receiver slots 30. Also, illustrated is post 32 connected at one end 34 to rigid support member 28. The opposite end 36 of post 32 is used for attachment of internal flexible mounting filling 26 and, thereby, unitary flexible male mold 24 to post 32. Unitary flexible male mold 24 may be connected through internal flexible mounting filling 26 to post 32 by any means known in the art such as allowing flexible mounting filling 26 to fill retaining holes 38, or by screws, glue, or any means now known or hereafter developed. Rigid support members 20 and 28 may be of any hard material capable of retaining shape during handling so that the rigid support members do not give or flex and so that only the flexible molds give and flex.

Figure 4:
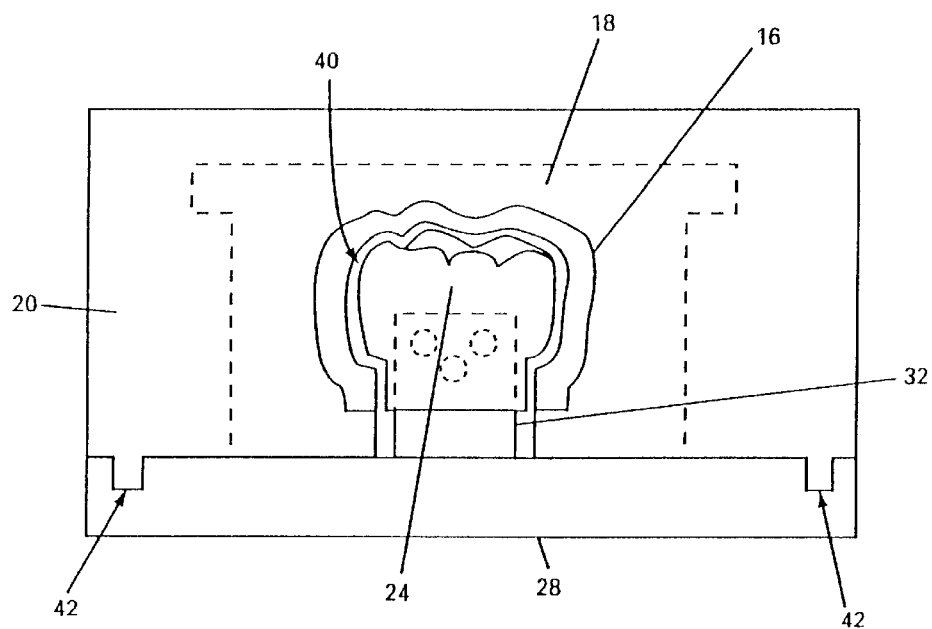
FIG. 4 is a side cross sectional view of the unitary flexible male mold joined with the unitary flexible female mold by the keyed joining of the two rigid support members.

Referring now to FIG. 4, unitary flexible male mold 24 is shown joined with unitary flexible female mold 16. While unitary flexible female mold 16 and unitary flexible male mold 24 essentially mirror each other, in a preferred embodiment of the invention, once placed together as illustrated in FIG. 4, they are held a predetermined distance apart from each other. In a further preferred embodiment, this distance is approximately 0.7 millimeters. Obviously, any appropriate distance for the thickness of the item being created is appropriate. In particular, in the field of dentistry, dental crowns of a thickness of approximately 0.7 millimeters is appropriate and useful. In any event, FIG. 4 illustrates that unitary flexible female mold 16 and unitary flexible male mold 24 are separated by a predetermined fixed amount 40 when the molds are pressed together.

FIG. 4 also illustrates the use of rigid support member 20 and rigid support member 28 in securing unitary flexible female mold 16 and unitary flexible male mold 24 in position. Importantly, FIG. 4 illustrates the use of key device 42. Key device 42 is formed by the combination of extended keys 22 and key receiver slots 30. In this manner, again, rigid support member 20 and rigid support member 28, and thereby unitary flexible female mold 16 and unitary flexible male mold 24, are held in the exact same position each time the molds are pressed together.

In operation, unitary flexible female mold 16 is created with reference to structure 10 so as, in any event, to reproduce complex external shape 12. Unitary flexible female mold 16 may be created directly from any suitable flexible material or in any other manner now known or hereafter developed. For example, one method of creating unitary flexible female mold 16 would be to hand carve, for example, structure 10. In the field of dentistry, structure 10 would represent a tooth exhibiting its various complex shapes. Once the complex external shape 12 of structure 10, i.e., the tooth, has been formed, structure 10 is hollowed out, for example, so as to create a mirror image, or substantially similar, complex internal shape 14. In this manner, then, a hard, hollow, custom model or die is created. Once created, unitary flexible female mold 16 is formed by the application of any suitable, flexible material now known or hereafter developed, such as silicone, and the like, to the exterior of structure 10 so as to create a unitary flexible mold 16 of complex external shape 12. Once the flexible material has set up, the unitary flexible female mold 16 can be removed from structure 10. Likewise, unitary flexible male mold 24 can be formed by making a mold of the complex internal shape 14 of structure 10. Again, this is merely one way of many by which these unitary flexible molds can be made. Unitary flexible male mold 24 can be carved, for example, out of flexible material, just as unitary flexible female mold 16 could be. In any event, once formed, any form making material now known or hereafter developed may be added to the unitary flexible female mold 16, for example, and unitary flexible male mold 24 inserted therein. As is known in the art, after a short period of time, the appropriate form making material hardens. At this point, it becomes necessary to separate the two molds. This is the point in the prior art, where the creation of complex external shapes created the need for splitting the female mold in order to remove the hardened material. Further, there was no way in the prior art that a complex internal shape could be created for the reason that the complex internal mold could not be removed once the material hardened. In this case, because Applicants' unitary flexible female mold 16 and unitary flexible male mold 24 are made of flexible, pliable, compressible material, unitary flexible male mold 24 can be easily removed from unitary flexible female mold 16 without damage to itself or the hardened material. Likewise, the hardened material can easily be removed from unitary flexible female mold 16 by bending unitary flexible female mold 16 away from the hardened material.

In a preferred embodiment, unitary flexible female mold 16 is encased in flexible mounting 18. Flexible mounting 18 is any flexible material, such as the same material of which the molds are made, which is flexible, compressible and bendable, and elastic. As a result, the edges of unitary flexible female mold 16 may be bent away from the hardened material and then the hardened material removed from unitary flexible female mold 16 without damage to the hardened material or to unitary flexible female mold 16.

Again, in a preferred embodiment, key device 42 is utilized so as to ensure that unitary flexible male mold 24 is consistently inserted within unitary flexible female mold 16 in the exact position and held the exact, predetermined, fixed distance 40 from unitary flexible female mold 16 so that a hardened complex structure of a desired thickness is created.

Also, it should be pointed out that there are many variations in the dentition of the human race. Various sizes of teeth exist. Factors, such as gender, race, and age, to name a few, cause teeth to be of different sizes. Therefore, it would be obvious that various sizes of the same tooth would necessitate different sizes of crowns for a dentist to use, requiring a die for each size.

By way of the invention a dentist, for example, can have available a full range of crowns for both children and adults. Further the invention enables the storing of anatomically correct crowns of naturally occurring external complexity that are easy to attach with minimum destruction of the tooth in preparation for receiving the crown because of the crown's authentic internal complexity.

As should also be obvious, once unitary flexible female mold 16 and unitary flexible male mold 24 have been formed, they may be used repeatedly so that any number of hardened structures identical to each other may be formed again and again. In particular, with regard to dentistry, this means that identical complex crowns can be made prior to the need for them. As a result, they may be stocked at a dentist's office and when the need arises for providing a crown for an adult tooth, for example, a mold of a particular tooth such as a molar for example, can be selected. The dentist no longer needs to remove healthy tooth from the patient since the mold fits essentially identically over the existing tooth structure. Very little "shaping" is required before a prefabricated high quality dental crown can be quickly assimilated in the patient's mouth. The advantages provided by Applicants' invention are significant in that heretofore, creations of crowns in a dental office in a short period of time typically did not enable the creation of structures that in any way resembled the physical anatomy of a normal human tooth. Further, most "quick fixes" use light cured materials. The utilization of light cured materials, as is known in the art, is fast but there are concurrent shrinkage problems and structural integrity problems associated with those materials in addition to the anatomical deficiencies already mentioned. All of these problems can be overcome since the crown structures created by way of Applicants' invention may be not only light but heat or oven cured or strengthened by any manner known in the art outside of the office, beforehand, without causing the patient to wait in discomfort while a crown is made.

While the apparatus and method of the present invention has been disclosed in connection with a preferred embodiment of dentistry, it should be clear that the apparatus and method can be used in other situations where the duplication of complex structures is required. This literally could be any industry, such as hardware, where complex machine parts have heretofore been created by hand. Thus, the apparatus and method for creating a structure with complex external and internal shapes of the present invention has the important advantage of providing a simple, repeatable, inexpensive method for creating such complex shapes.

While the present invention has been disclosed in connection with the preferred embodiment thereof, it should be understood that there may be other embodiments which fall within the spirit and scope of the invention as defined by the following claims.

What is claimed is:

1. An apparatus for creating a structure with complex external and internal shapes comprising:
    (a) a unitary flexible female mold of a structure with complex external shapes;
    (b) a unitary flexible male mold of the interior of said structure with complex internal shapes that essentially mirror said complex external shapes; and
    (c) a keying device connected to said molds so that said unitary flexible female mold and said unitary flexible male mold are maintained in a predetermined fixed relationship when pressed together.

2. The apparatus of claim 1 further comprising rigid support members connected to said unitary flexible female mold and said unitary flexible male mold.

3. The apparatus of claim 2 wherein the unitary flexible male mold further comprises an internal flexible mounting filling for attachment to said rigid support member.

4. The apparatus of claim 3 wherein said unitary flexible male mold further comprises:
    (a) a post connected to said rigid support member at a first end; and
    (b) the unitary flexible male mold attached to a second end of said post.

5. The apparatus of claim 1 wherein said complex shapes further comprise a combination of convex and concave shapes.

6. The apparatus of claim 1 wherein the unitary flexible female mold further comprises a surrounding flexible mounting for flexible attachment of said unitary flexible female mold to said rigid support member.

7. The apparatus of claim 1 wherein said fixed relationship of said molds results in an approximate 0.7 millimeter separation of said molds.

8. In the field of dentistry wherein it is necessary to cover an existing tooth with a crown while preserving as much of the tooth as possible, an apparatus for forming a crown with complex external and internal shapes comprising:
    (a) a unitary flexible female mold of a tooth with complex external shapes;
    (b) a unitary flexible male mold of the interior of said tooth with complex internal shapes that mirror said complex exterior shapes; and
    (c) a keying device in said unitary flexible female mold and said unitary flexible male mold so that the molds are maintained in a predetermined fixed relationship when pressed together.

9. The apparatus of claim 8 further comprising rigid support members connected to said unitary flexible female mold and said unitary flexible male mold.

10. The apparatus of claim 9 wherein the unitary flexible female mold further comprises a surrounding flexible mounting for flexible attachment of said unitary flexible female mold to said rigid support member.

11. The apparatus of claim 9 wherein the unitary flexible male mold further comprises an internal flexible mounting filling for attachment to said rigid support member.

12. The apparatus of claim 11 wherein said unitary flexible male mold further comprises:
    (a) a post connected to said rigid support member at a first end; and
    (b) the unitary flexible male mold attached to a second end of said post.

13. The apparatus of claim 9 wherein said fixed relationship of said molds results in an approximate 0.7 millimeter separation of said molds.

14. The apparatus of claim 8 wherein said complex shapes further comprise a combination of convex and concave shapes.

15. A method for creating a structure with complex external and internal shapes comprising the steps of:
    (a) forming a unitary flexible female mold of a structure with complex external shapes;
    (b) forming a unitary flexible male mold of the interior of said structure with complex internal shapes mirroring said complex external shapes;
    (c) providing a keying device in said molds so that said unitary flexible female mold and said unitary flexible male mold are maintained in a predetermined fixed relationship when pressed together;
    (d) applying forming material to said molds;
    (e) pressing said molds together in said predetermined fixed relationship; and
    (f) separating said molds and removing said forming material once hardened.

16. The method of claim 15 further comprising the step of attaching said unitary flexible female mold and said unitary flexible male mold to rigid support members.

17. The method of claim 16 wherein the step of forming a unitary flexible female mold further comprises the step of surrounding said unitary flexible female mold with a flexible mounting for flexible attachment to said rigid support member.

18. The method of claim 16 wherein the step of forming a unitary flexible male mold further comprises the step of filling the interior of the unitary flexible male mold with a flexible mounting for attachment to said rigid support member.

19. The method of claim 18 wherein the step of connecting said unitary flexible male mold to a rigid support member further comprises the steps of:

(a) connecting a first end of a post to said rigid support member; and (b) attaching the unitary flexible male mold to a second end of said post.

20. The method of claim 15 wherein the step of forming molds with complex shapes further comprises creating complex shapes in the form of a combination of convex and concave shapes.

* * * * *